(12) United States Patent
Ishiguro et al.

(10) Patent No.: US 10,842,396 B2
(45) Date of Patent: Nov. 24, 2020

(54) VIBRATION WAVEFORM SENSOR AND WAVEFORM ANALYSIS DEVICE

(71) Applicant: TAIYO YUDEN CO., LTD., Tokyo (JP)

(72) Inventors: Takashi Ishiguro, Takasaki (JP); Keiichi Kobayashi, Takasaki (JP); Yutaka Aoki, Takasaki (JP)

(73) Assignee: TAIYO YUDEN CO., LTD., Tokyo (JP)

( * ) Notice: Subject to any disclaimer, the term of this patent is extended or adjusted under 35 U.S.C. 154(b) by 271 days.

(21) Appl. No.: 15/566,666

(22) PCT Filed: Apr. 9, 2016

(86) PCT No.: PCT/JP2016/061629
§ 371 (c)(1),
(2) Date: Oct. 13, 2017

(87) PCT Pub. No.: WO2016/167202
PCT Pub. Date: Oct. 20, 2016

(65) Prior Publication Data
US 2018/0092556 A1    Apr. 5, 2018

(30) Foreign Application Priority Data

Apr. 17, 2015   (JP) ................................. 2015-085184

(51) Int. Cl.
*A61B 5/00*   (2006.01)
*A61B 5/024*   (2006.01)
(Continued)

(52) U.S. Cl.
CPC .......... *A61B 5/02444* (2013.01); *A61B 5/026* (2013.01); *A61B 5/02007* (2013.01);
(Continued)

(58) Field of Classification Search
CPC ..... G06F 3/016; G06F 21/32; A61B 5/02405; A61B 5/6802; A61B 2017/00106;
(Continued)

(56) References Cited

U.S. PATENT DOCUMENTS

| 4,784,152 A | * | 11/1988 | Shinoda | ................. | A61B 5/021 |
| | | | | | 600/503 |
| 5,904,654 A | * | 5/1999 | Wohltmann | ....... | A61B 5/02007 |
| | | | | | 600/481 |

(Continued)

FOREIGN PATENT DOCUMENTS

| CN | 1195277 A | 10/1998 |
| CN | 1792319 A | 6/2006 |

(Continued)

OTHER PUBLICATIONS

International Search Report (ISR) dated Jul. 12, 2016, issued for International application No. PCT/JP2016/061629.

(Continued)

*Primary Examiner* — May A Abouelela
(74) *Attorney, Agent, or Firm* — Law Office of Katsuhiro Arai

(57) ABSTRACT

In an embodiment, a sensor module 10 includes a piezoelectric element 30 placed on the principal face of a board 20, which piezoelectric element is surrounded by a vibration ring 40 and installed in an appropriate position on a person's arm, neck, etc., using a medical fixing tape, etc., with the vibration ring 40 contacting the person's skin. When a pulse wave is transmitted to the vibration ring 40 from the skin, the board 20 also vibrates and this vibration is transmitted to the piezoelectric element 30. Then, the piezoelectric element 30 is displaced and the pulse wave vibration is converted to an electrical signal. The resulting electrical signal is amplified by an amplifier on the board 20 and input to the vibration analysis device 100, where prescribed calculations are run to (Continued)

perform waveform analysis. The vascular state, etc., can be known from pulse waveforms.

15 Claims, 10 Drawing Sheets

(51) Int. Cl.
| | |
|---|---|
| A61B 5/02 | (2006.01) |
| A61B 5/026 | (2006.01) |
| A61B 5/11 | (2006.01) |
| A61B 5/0245 | (2006.01) |
| G01H 11/08 | (2006.01) |
| A61B 5/0464 | (2006.01) |
| A61B 5/0205 | (2006.01) |

(52) U.S. Cl.
CPC ........ *A61B 5/0245* (2013.01); *A61B 5/02438* (2013.01); *A61B 5/1102* (2013.01); *A61B 5/6831* (2013.01); *A61B 5/6833* (2013.01); *G01H 11/08* (2013.01); *A61B 5/0205* (2013.01); *A61B 5/0464* (2013.01); *A61B 2562/0204* (2013.01); *A61B 2562/0219* (2013.01)

(58) Field of Classification Search
CPC ..... A61B 2090/378; A61B 5/742; A61B 8/00; A61B 17/22012; A61B 17/2202; A61B 17/320068; A61B 2034/2063; A61B 5/0205; A61B 5/021; A61B 5/024
USPC .................. 600/300, 500, 503, 481; 381/67; 310/334
See application file for complete search history.

(56) References Cited

U.S. PATENT DOCUMENTS

| | | | |
|---|---|---|---|
| 6,095,984 A | 8/2000 | Amano et al. | |
| 6,241,684 B1* | 6/2001 | Amano | A61B 5/02438 600/503 |
| 6,371,920 B1* | 4/2002 | Kamimoto | A61B 8/02 600/438 |
| 6,491,647 B1* | 12/2002 | Bridger | A61B 5/021 128/900 |
| 7,341,561 B2* | 3/2008 | Tanaka | A61B 5/02438 600/344 |
| 7,436,102 B2* | 10/2008 | Fujii | H03H 3/02 310/320 |
| 8,657,748 B2* | 2/2014 | Nitta | A61B 5/02007 600/437 |
| 8,755,535 B2* | 6/2014 | Telfort | A61B 7/003 381/67 |
| 9,924,881 B2* | 3/2018 | Fujii | A61B 5/02422 |
| 2002/0013534 A1* | 1/2002 | Muramatsu | A61B 5/02438 600/503 |
| 2004/0032957 A1* | 2/2004 | Mansy | A61B 5/04085 381/67 |
| 2005/0124864 A1* | 6/2005 | Mack | A61B 5/024 600/300 |
| 2005/0200242 A1* | 9/2005 | Degertekin | B06B 1/0292 310/334 |
| 2006/0186762 A1* | 8/2006 | Sugiura | H03H 9/588 310/328 |
| 2007/0269060 A1* | 11/2007 | Chou | H04R 1/46 381/174 |
| 2008/0037808 A1* | 2/2008 | Sawada | B06B 1/0622 381/190 |
| 2008/0174207 A1* | 7/2008 | Tsuda | H03H 3/08 310/334 |
| 2008/0218030 A1* | 9/2008 | Asada | G10K 9/122 310/334 |
| 2008/0219464 A1* | 9/2008 | Smith | G10K 15/02 381/67 |
| 2008/0238259 A1* | 10/2008 | Osawa | B06B 1/0611 310/334 |
| 2010/0274099 A1* | 10/2010 | Telfort | A61B 5/6843 600/300 |
| 2011/0077537 A1* | 3/2011 | Ebara | A61B 5/0245 600/500 |
| 2012/0197140 A1* | 8/2012 | Okuda | A61B 5/02007 600/500 |
| 2013/0006123 A1* | 1/2013 | Aoshima | A61B 5/02438 600/483 |
| 2013/0066218 A1* | 3/2013 | Kim | A61B 5/0245 600/500 |
| 2014/0103781 A1* | 4/2014 | Nakamura | H01L 41/09 310/334 |
| 2014/0265727 A1* | 9/2014 | Berte | B06B 1/0603 310/317 |
| 2014/0285068 A1* | 9/2014 | Shibata | H01L 41/0805 310/334 |
| 2015/0138281 A1* | 5/2015 | Kitada | B41J 2/14201 347/68 |
| 2015/0141774 A1 | 5/2015 | Ogawa et al. | |
| 2015/0214466 A1* | 7/2015 | Park | G06F 3/016 310/324 |
| 2015/0258574 A1* | 9/2015 | Lin | B06B 1/0644 310/334 |
| 2015/0266059 A1* | 9/2015 | Kubo | B06B 1/0622 310/334 |
| 2015/0368161 A1* | 12/2015 | Murakami | B41J 2/14233 252/62.9 PZ |
| 2016/0008851 A1* | 1/2016 | Tajitsu | H01L 41/45 381/190 |
| 2016/0023245 A1* | 1/2016 | Zadesky | A61B 5/7455 310/334 |
| 2016/0172578 A1* | 6/2016 | Valbin | A61B 5/02444 600/508 |

FOREIGN PATENT DOCUMENTS

| | | |
|---|---|---|
| CN | 101726387 A | 6/2010 |
| CN | 104507384 A | 4/2015 |
| JP | 2004514116 A | 5/2004 |
| JP | 2007125366 A | 5/2007 |
| JP | 2009034427 A | 2/2009 |
| JP | 2014042579 A | 3/2014 |
| TW | 201347728 A | 12/2013 |
| TW | M493363 U | 1/2015 |
| WO | 9738626 A1 | 10/1997 |
| WO | 0228274 A1 | 8/2001 |
| WO | 2013145352 A1 | 10/2013 |

OTHER PUBLICATIONS

A Notification of Examination Opinions with Search Report issued by Taiwan Intellectual Property Office, dated Feb. 27, 2020, for Taiwan counterpart application No. 105133507. (8 pages).
A First Office Action issued by the State Intellectual Property Office of China dated Oct. 9, 2019 for Chinese counterpart application 201680022353.9 (9 pages).
A Notification of Reasons for Refusal issued by the Japanese Patent Office, dated Jan. 31, 2020, for Japanese counterpart application No. 2017-512517. (5 pages).

* cited by examiner

[FIG. 1]
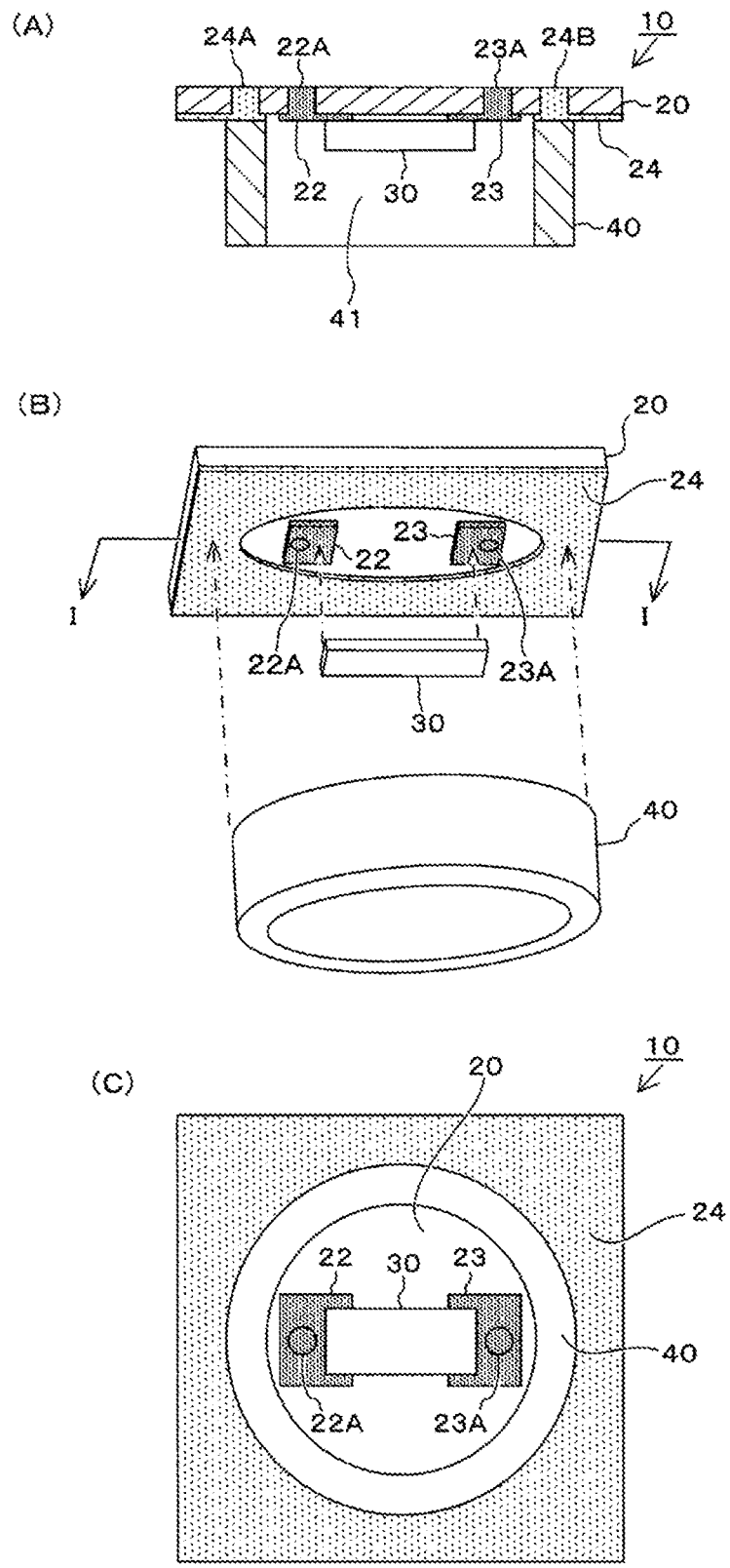

[FIG. 2]
(A)
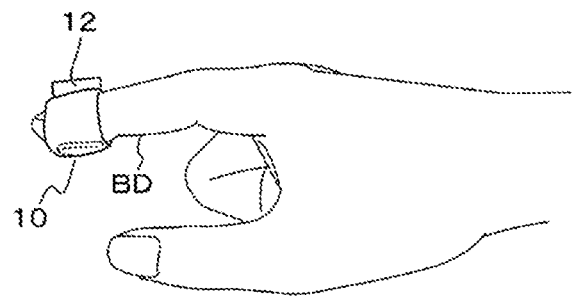
(B)
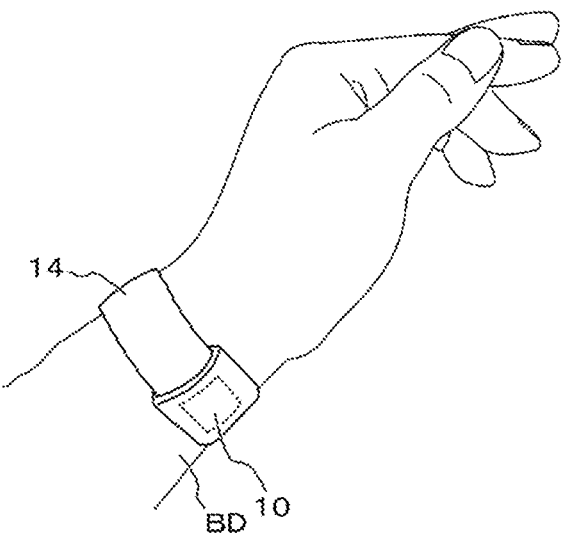
(C)
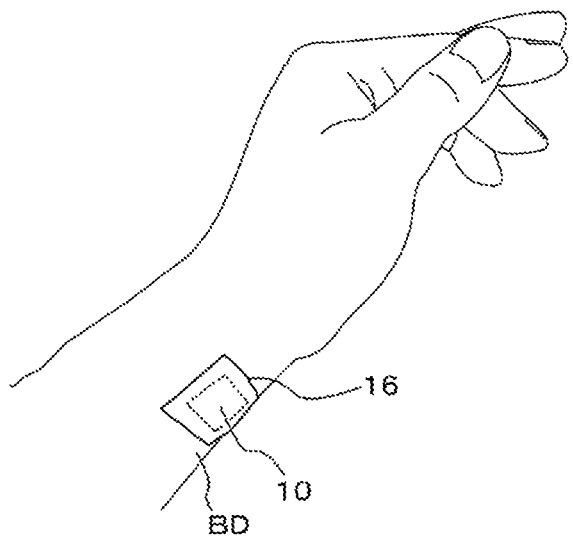

[FIG. 3]
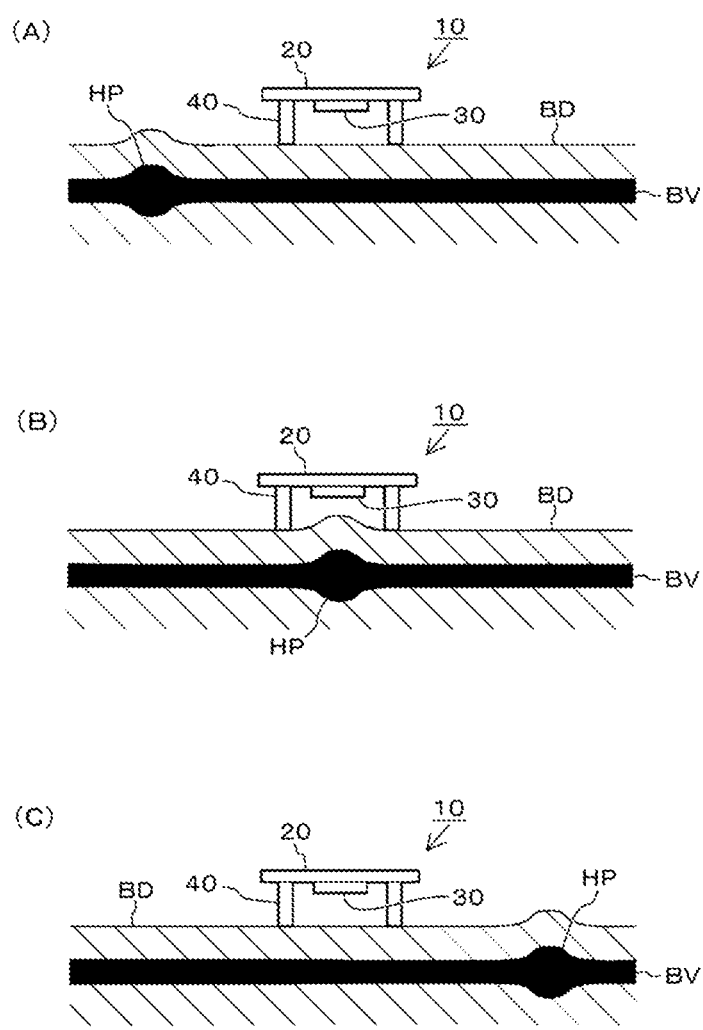

[FIG. 4]
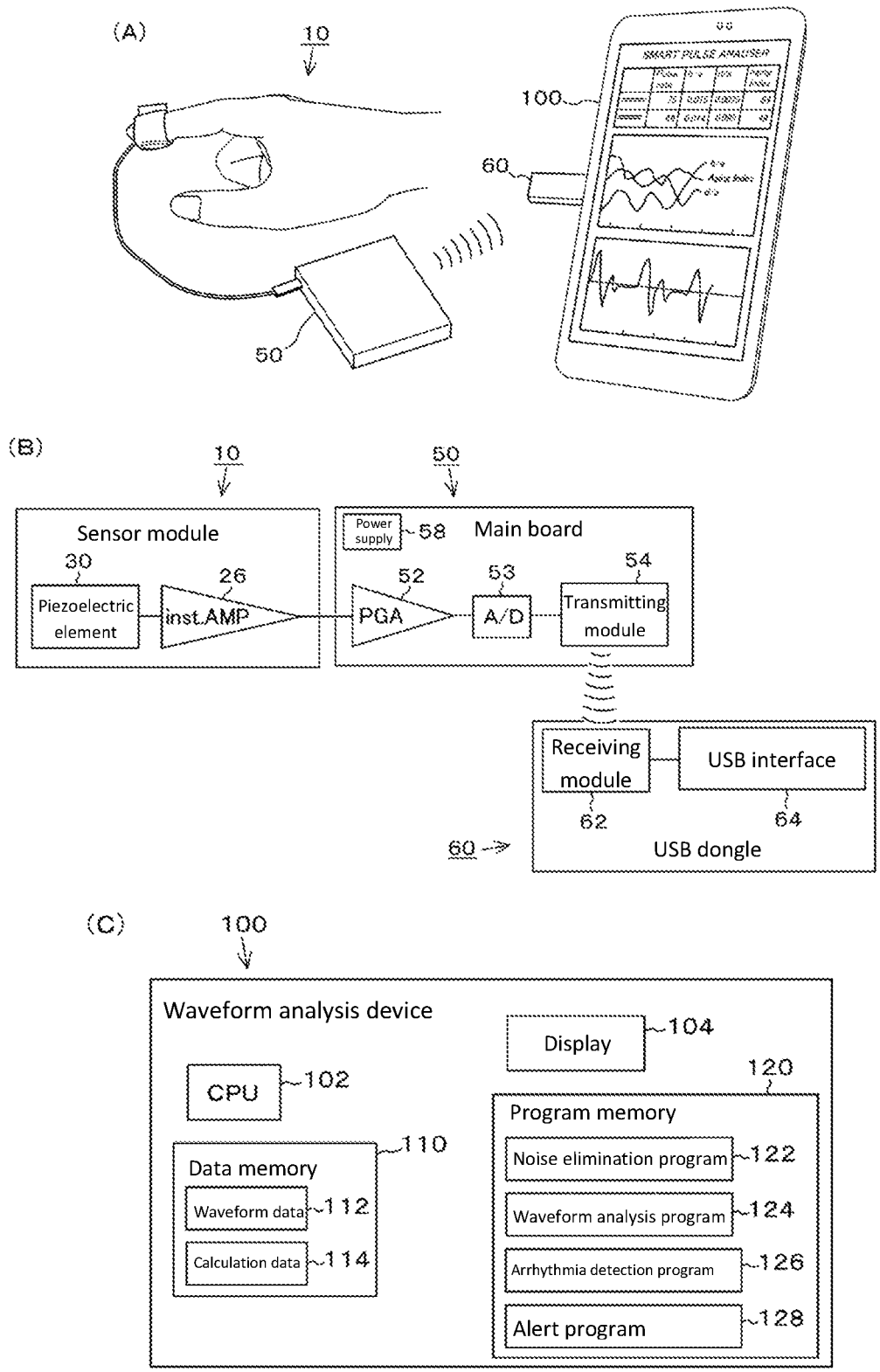

[FIG. 5]
(A)
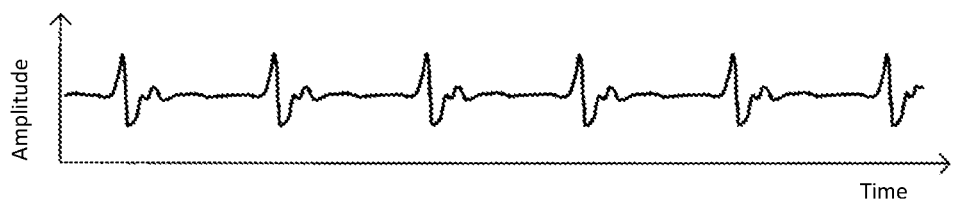
(B)
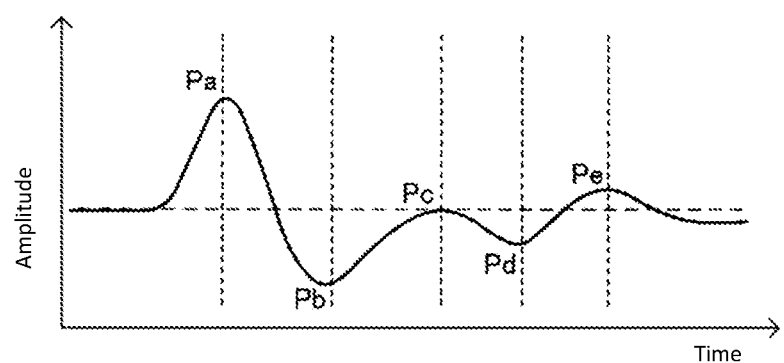
(C)
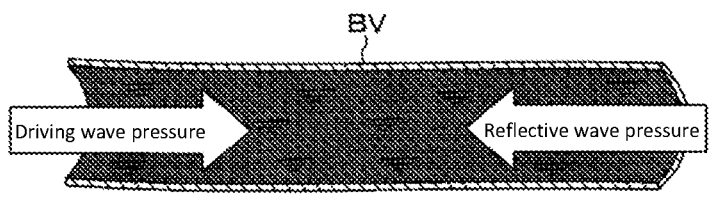
(D)

[FIG. 6]

| Setting | |
|---|---|
| Display Pulse Rate Graph | ☑ |
| Display b/a Graph | ☑ |
| Display c/a Graph | ☑ |
| ⋮ | |
| Sound Beep | ☑ |
| Flash Screen | ☑ |
| Automatically Save Brain Wave Data | ☑ |
| Automatically Save Calculation Data | ☑ |
| ⋮ | |
| Pulse High Threshold (bpm)<br>80bpm | ☑ |
| Pulse Low Threshold (bpm)<br>50bpm | ☑ |
| b/a High Threshold<br>1.0 | ☑ |
| b/a Low Threshold<br>-1.0 | ☑ |
| c/a High Threshold<br>1.0 | ☑ |

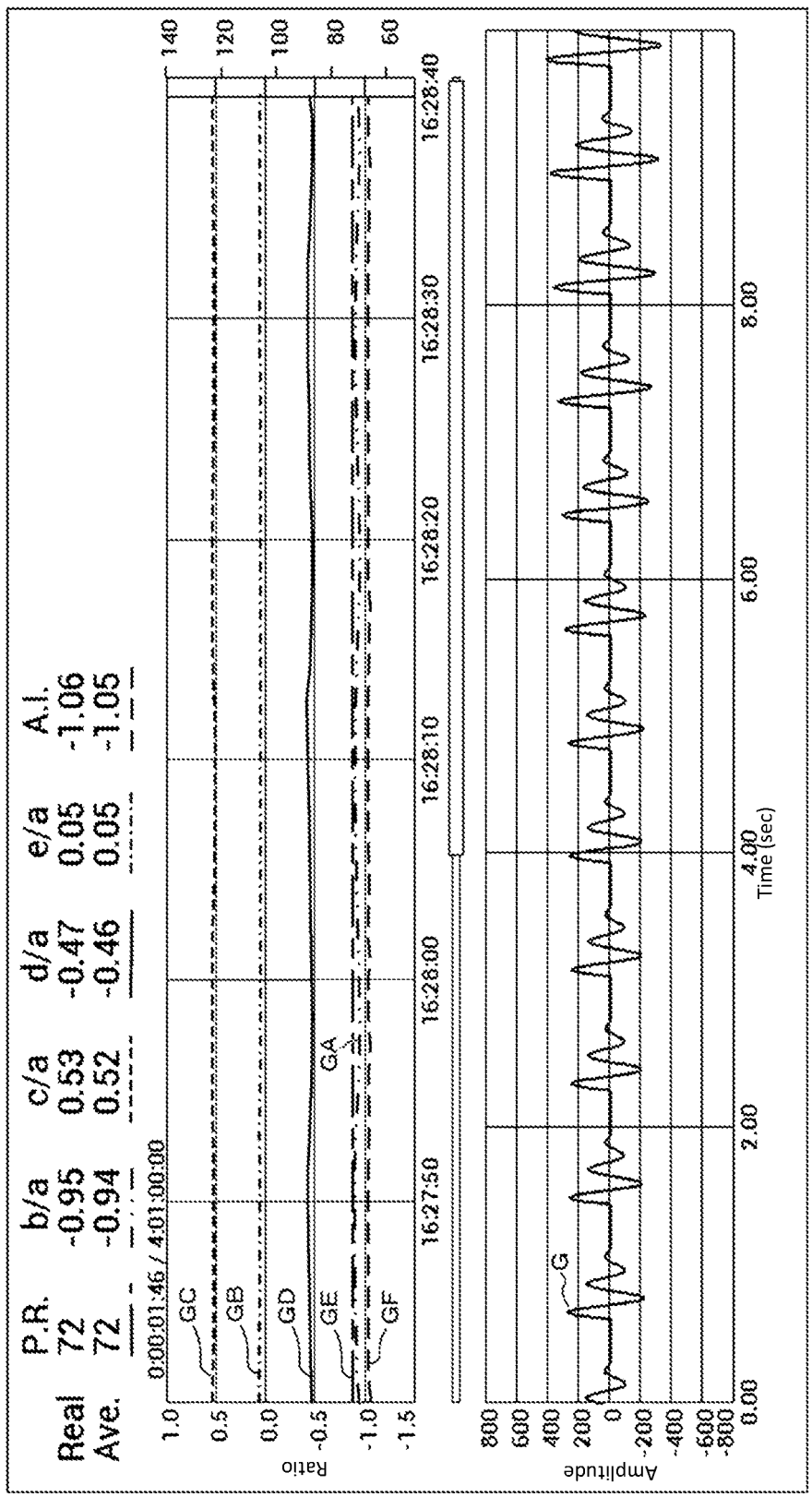
[FIG. 7]

[FIG. 8]
(A)
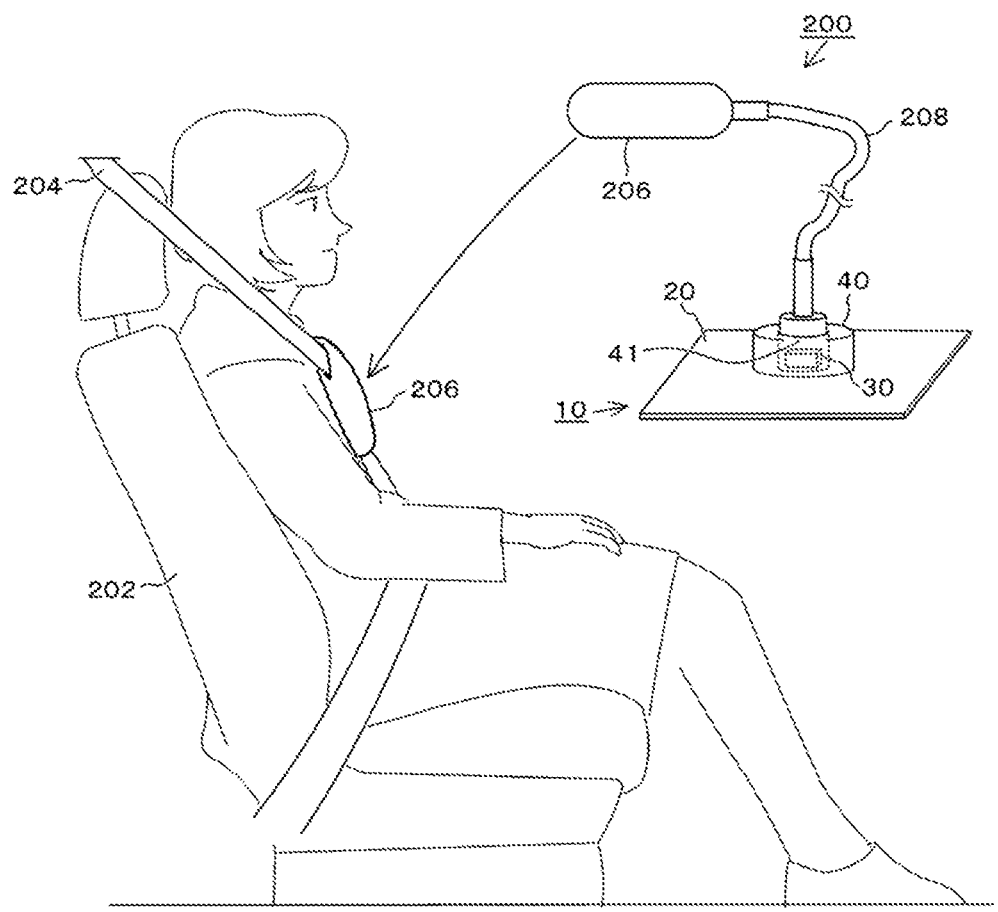
(B)
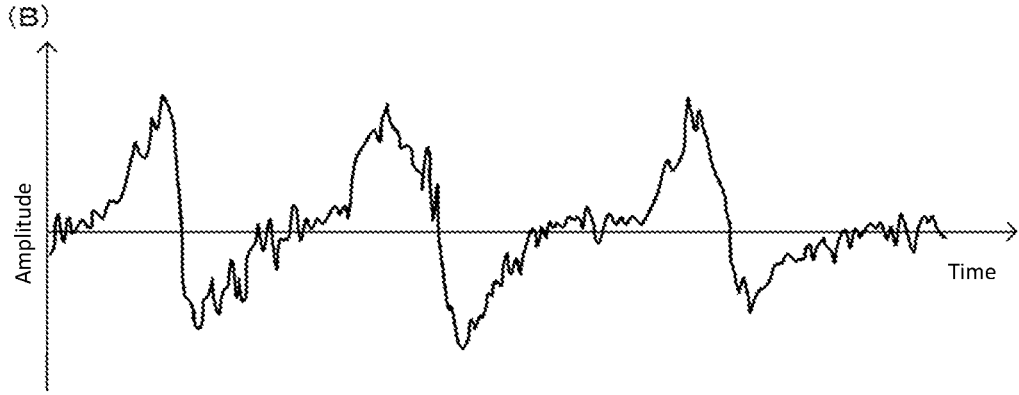

[FIG. 9]
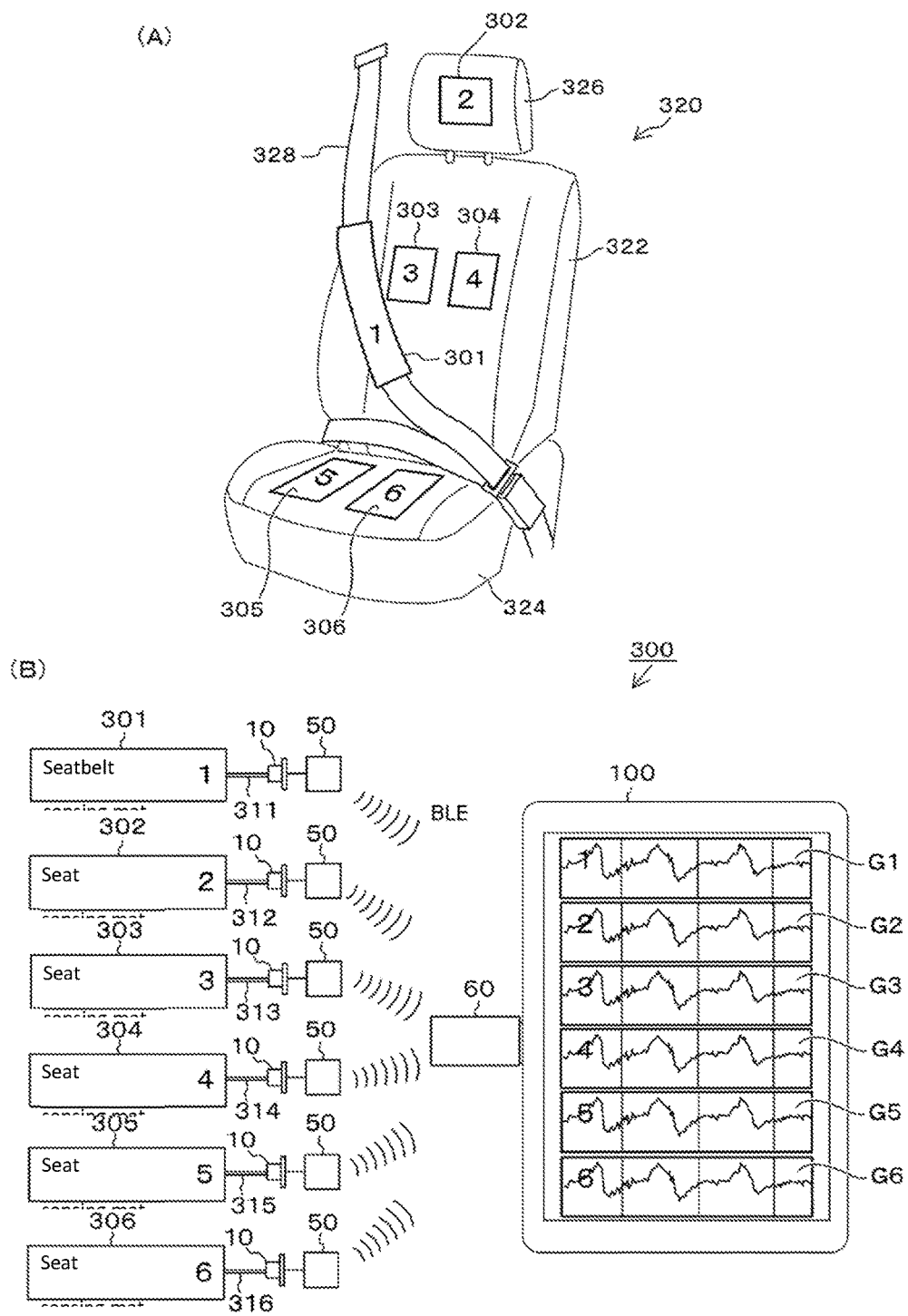

[FIG. 10]
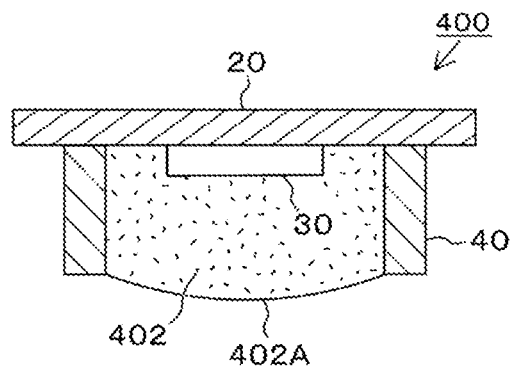
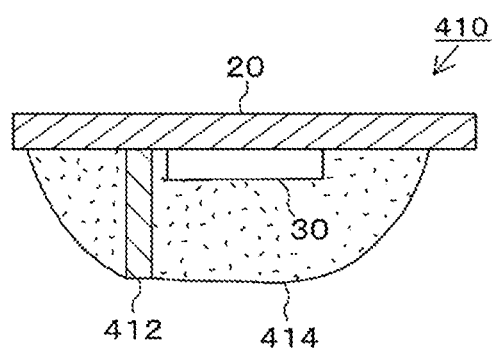
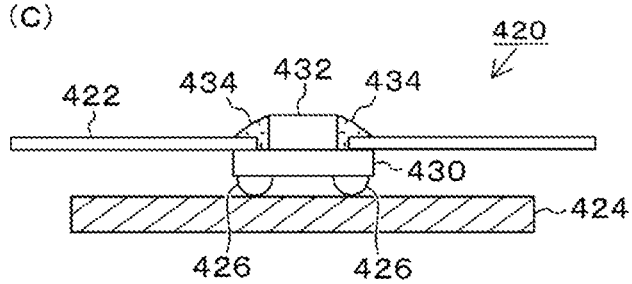

VIBRATION WAVEFORM SENSOR AND WAVEFORM ANALYSIS DEVICE

This application is the U.S. National Phase under 35 U.S.C. § 371 of International Application PCT/JP2016/061629, filed Apr. 9, 2016, which claims priority to Japanese Patent Application No. 2015-085184, filed Apr. 17, 2015. The International Application was published under PCT Article 21(2) in a language other than English.

The present invention relates to an improved vibration waveform sensor that measures the waveforms of various vibrations such as pulse beats, and waveform analysis device that analyzes the waveforms thus obtained.

BACKGROUND ART

For example, pulse oximeters are known as devices that measure human pulse waves (waveforms of pulses). A pulse oximeter detects bulging of a blood vessel caused by the vibrations of the wall of the blood vessel, based on the amount of LED (light-emitting diode) light absorbed by hemoglobin in the blood in the blood vessel. This way, blood oxygen levels and volume pulse waveforms can be obtained. Examples of prior art relating to pulse oximeters are described in the following patent literatures.

BACKGROUND ART LITERATURE

Patent Literature

Patent Literature 1: Japanese Translation of PCT International Patent Laid-open No. 2004-514116
Patent Literature 2: Japanese Patent Laid-open No. 2009-34427

SUMMARY OF THE INVENTION

Problems to be Solved by the Invention

The aforementioned prior art uses light which is continuously output from an LED and therefore consumes a large amount of power at the mW level, and consequently it is not suitable for wearable devices intended for continuous measurement. In addition, the prior art, although capable of obtaining the volume waveforms of pulse waves, does not necessarily provide high enough resolution.

On the other hand, the ability to continuously measure pulse acceleration waveforms is very convenient, because then it is possible to know the state of arterial sclerosis or level of stress of the patient, and also understand changes in the vascular condition of the patient during and after surgery or after drug administration. However, the process of detecting pulses and displaying pulse waves involves averaging, waveform shaping, and two-step differential calculations, and thus takes a considerably long time (approx. 10 to 5 msec).

The present invention was developed in light of these points, and an object of the present invention is to continuously measure, and also analyze, vibration waveforms. Another object is to measure vibration waveforms in a favorable manner while keeping the power consumption low. Yet another object is to achieve vibration waveform measurement suitable for wearable applications.

Means for Solving the Problems

A vibration waveform sensor according to the present invention is characterized in that it comprises: a circuit board; a piezoelectric element provided on the circuit board, that continuously measures the vibrations of the circuit board to obtain vibration waveforms; and a vibration-conveying body that contacts a target and transmits its vibrations to the circuit board.

Another vibration waveform sensor according to the present invention is characterized in that it comprises: a circuit board that transmits vibrations; a piezoelectric element installed on the circuit board, that converts the vibrations transmitted from the circuit board to electrical signals and outputs them as waveform signals to obtain vibration waveforms; and a vibration-conveying body that contacts a target, introduces its vibrations, and transmits them to the circuit board.

One key mode of the present invention is characterized in that the vibration-conveying body is conductive. Another mode of the present invention is characterized in that a signal amplification means for amplifying the waveform signals output from the piezoelectric element, is provided on the circuit board. Yet another mode of the present invention is characterized in that the vibration-conveying body is a conductive ring with a resin molded in such a way that it fills the space inside the ring and also bulges out of the ring. Yet another mode of the present invention is characterized in that the circuit board also serves as the vibration-conveying body. Yet another mode of the present invention is characterized in that the piezoelectric element is shaped in such a way that it has a longitudinal direction, and that the piezoelectric element outputs the waveform signals based primarily on displacement in the longitudinal direction.

A waveform analysis device according to the present invention is characterized in that it performs predefined calculations with respect to the vibration waveforms obtained by any of the aforementioned vibration waveform sensors, to conduct waveform analysis. One key mode of the present invention is characterized in that the vibration waveforms are human pulse waveforms, and that the early systolic positive wave height Pa, early systolic negative wave height Pb, mid-systolic re-ascending wave height Pc, late systolic re-descending wave height Pd, and early diastolic positive wave height Pe are detected from these waveforms, while at least one of the Pb/Pa, Pc/Pa, Pd/Pa, Pe/Pa, and (Pb−Pc−Pd−Pe)/Pa is calculated using these values.

Another mode of the present invention is characterized in that it includes a noise elimination means for eliminating, as noise, the peak values of the vibration waveforms when they exceed a preset threshold. Yet another mode of the present invention is characterized in that, when the aforementioned vibration waveforms are pulse waves, it includes: a waveform analysis means for performing prescribed calculations with respect to each of the multiple waveform components included in the pulse waves; an arrhythmia detection means for detecting arrhythmia from the pulse intervals of the pulse waves; and an alarm means for outputting an alarm when the result of calculations by the waveform analysis means exceeds a prescribed threshold or when arrhythmia is detected by the arrhythmia detection means. The aforementioned and other objects, characteristics, and benefits of the present invention are made clear by the detailed explanations below and the drawings attached hereto.

Effects of the Invention

According to the present invention, vibrations of the target are introduced by the vibration-conveying body into the circuit board on which the piezoelectric element is installed; accordingly, vibration waveforms of the target can be measured continuously with the piezoelectric element while keeping the power consumption low, which is suitable for small, wearable devices.

BRIEF DESCRIPTION OF THE DRAWINGS

FIG. 1 Drawings showing the sensor module in Example 1 of the present invention. (A) is a cross-sectional view, (B) is an assembly drawing, and (C) is a view from the principal face, of the sensor module.

FIG. 2 Drawings showing the sensor module in Example 1 above, as it is installed on a person's finger and arm.

FIG. 3 Drawings showing how a pulse moves and the skin vibrates.

FIG. 4 Drawings showing the constitution of Example 2 of the present invention. (A) shows an overall device constitution, while (B) and (C) show circuit constitutions.

FIG. 5 Drawings showing examples of measured pulse waves.

FIG. 6 Drawing showing an example of a setting menu on the waveform analysis device in Example 2.

FIG. 7 Drawing showing an example of how analysis results are displayed on the waveform analysis device in Example 2.

FIG. 8 Drawings showing Example 3 where the present invention is applied to breath sensing. (A) shows its constitution, while (B) shows an example of measured waveforms.

FIG. 9 Drawings showing Example 4 where the present invention is applied to seated sensing. (A) shows an example of sensor layout, while (B) shows a device constitution.

FIG. 10 Drawings showing Example 5 of the present invention. (A) and (B) show other constitutional examples of the sensor module, while (C) shows an example of how the sensor module is installed.

MODE FOR CARRYING OUT THE INVENTION

The best modes for carrying out the present invention are explained in detail below based on the examples.

Example 1

First, an example of a vibration waveform sensor according to the present invention is explained by referring to FIGS. 1 to 3. In FIG. 1, how the present invention is used as a pulse wave sensor is shown. FIG. 1 (A) shows a cross-sectional view, FIG. 1 (B) shows an exploded view, and FIG. 1 (C) shows a view from the bottom face, of a sensor module 10. In these drawings, the sensor module 10 is structured in such a way that a piezoelectric element 30 is placed on the principal face of a board 20, and the piezoelectric element 30 is surrounded by a vibration ring 40. The piezoelectric element 30 is rectangular, as shown in FIG. 1 (C), and has a longitudinal direction.

Among the respective parts mentioned above, the board 20 is used to fix and support the piezoelectric element 30, and also lead out its electrodes and amplify its signals, and is formed by glass epoxy, ceramics, etc. On the principal face of the board 20, a pair of electrode lands 22, 23 are provided near the center, and a ground conductor 24 is formed around them. The electrode lands 22, 23 are led out to the reverse side of the board 20 via through holes 22A, 23A. Terminals (not illustrated) of the piezoelectric element 30 are bonded to the electrode lands 22, 23 using conductive adhesive, etc. This way, the piezoelectric element 30 is connected to an amplifier (described later), etc., provided on the reverse side of the board 20 by means of the electrode lands 22, 23 and through holes 22A, 23A. For the piezoelectric element 30, PZT (lead zirconate titanate) is used, for example. Also, an insulating resin may be provided in a manner covering the electrode lands 22, 23. In this case, the piezoelectric element 30 may also be covered with the resin.

Next, the vibration ring 40 is provided in a manner surrounding the piezoelectric element 30, and the vibration ring 40 is electrically connected to the ground conductor 24. Also, the ground conductor 24 is led out to the reverse side of the board 20 via the through holes 24A, 24B (shown only in FIG. 1 (A)). The vibration ring 40 is formed by stainless steel, for example, and is conductive, has the same ground potential as the human skin it is contacting, and also functions as a vibration-conveying body that introduces vibrations of the skin and transmits them to the board 20. The vibrations of the skin are transmitted to the vibration ring 40, and also transmitted to the board 20 from the vibration ring 40. The board 20 also functions as a vibrator, so that the vibrations transmitted from the vibration ring 40 are transmitted to the piezoelectric element 30. A cavity 41 is formed by this vibration ring 40.

As shown in FIG. 2, the sensor module 10 described above is installed in an appropriate position on a person's arm, neck, etc., using a medical fixing tape, etc., in such a way that the vibration ring 40 contacts the person's skin BD. FIG. 2 (A) shows the module installed on a fingertip with a medical fixing tape 12, FIG. 2 (B) shows the module wrapped around an arm using a surface fastener 14, and FIG. 2 (C) shows the module attached to an arm with a medical fixing tape 16.

Next, the basic operations of the sensor module 10 are explained by referring to FIG. 3. FIGS. 3 (A) to 3 (C) show how a pulse wave transmits through a blood vessel BV in a human body. A pulse wave is a volume change, captured as a waveform from the body surface, that occurs in a given part of body tissue as blood flows into the part due to the beating of the heart. It should be noted that, in FIG. 3, a part of the blood vessel BV with a large volume is denoted by HP, and a pulse wave transmits from the left to the right. The pulse wave is transmitted to the vibration ring 40 of the sensor module 10 via the skin BD. As the vibration ring 40 vibrates, the board 20 also vibrates and this vibration is transmitted to the piezoelectric element 30. Then, the piezoelectric element 30 displaces and the pulse wave vibration is converted to an electrical signal. The resulting electrical signal is amplified by an amplifier on the board 20 and output. It should be noted that the output waveform signal is based primarily on the displacement of the piezoelectric element 30 in the lengthwise direction (longitudinal direction). FIG. 5 (A) shows an example of measured pulse waves. By its very nature, the piezoelectric element 30 detects pulse wave accelerations.

As described above, in this example the piezoelectric element 30 is installed on the board 20 that also functions as a vibrator, and vibrations of the skin BD are transmitted to the board 20 via the vibration ring 40, and accordingly pulse waves HP can be detected in a favorable manner. Also, use of the piezoelectric element 30 presents a benefit in that it permits direct measurement of acceleration pulse waves at high resolution, which means that there is no need for two-step differential calculations unlike when optical methods such as the aforementioned pulse oximeters are used, and therefore pulse waves HP can be measured continuously while keeping the power consumption low. Furthermore, the vibration ring 40 has the same ground potential as the skin BD, which means that effect of noise is reduced. It should be noted that, although this example was explained in the context of detecting pulse wave accelerations, "pulse wave speeds" can also be detected with relatively easy calculations involving only one differential calculation step.

Example 2

Next, a waveform analysis system using the aforementioned sensor module 10 is explained by referring to FIGS. 4 to 7. FIG. 4 (A) shows an overall constitution, where the sensor module 10 is connected to a main board 50 and the main board 50 is connected to a waveform analysis device 100 via a USB (Universal Serial Bus) dongle 60 for wireless communications.

FIG. 4 (B) shows the circuit constitution of each part. The sensor module 10 is such that the output side of the piezoelectric element 30 is connected to the input side of an instrumentation amplifier (operational amplifier with high input impedance) 26 provided on the reverse side of the board 20, and an output from this instrumentation amplifier 26 is connected to the input side of the main board 50 as an output of the sensor module 10.

A programmable amplifier 52 is provided on the input side of the main board 50, and its output side is connected to a transmitting module 54 via an A/D converter 53. In other words, pulse waveform signals that have been amplified by the programmable amplifier 52 are converted to digital signals through the A/D converter 53, and transmitted from the transmitting module 54. For the transmitting module 54, one conforming to any of the various known standards for near distance radio communications using radio waves or infrared light, may be used. For example, a transmitting module conforming to the BLE (Bluetooth® Low Energy) or other standard for low-power communications is used. A button battery or other power supply 58 is provided on the main board 50, from which drive power is supplied to each part of the main board 50 and also to the sensor module 10.

The USB dongle 60 is used so that the waveform analysis device 100 can capture the signals transmitted from the main board 50, and has a receiving module 62 and a USB interface 64. It should be noted that the USB dongle 60 is not required so long as the waveform analysis device 100 can directly receive the signals transmitted from the main board 50. The USB dongle 60 is also used in the control of main board 50 operations by the waveform analysis device 100.

Next, the waveform analysis device 100 is constituted by a PC (personal computer), smartphone, tablet PC, etc., and as shown in FIG. 4 (C), it has a CPU 102, a data memory 110, a program memory 120, and a display 104. Programs stored in the program memory 120 are run by the CPU 102. As the programs are run, the data stored in the data memory 110 are referenced. The calculation results are stored in the data memory 110 and also shown on the display 104. These basic operations are general in nature and all of them are known.

Waveform data 112 received by the USB dongle 60 are stored in the data memory 110. Calculation data 114 representing the calculation results by the CPU 102 are also stored. A noise elimination program 122, a waveform analysis program 124, an arrhythmia detection program 126, and an alert program 128, are provided in the program memory 120. In the case of a smartphone, these programs are provided as apps.

Among the above, the noise elimination program 122 is a program designed to eliminate the noise contained in the waveform data 112 by implementing signal processing so that, when the peak value of a pulse wave exceeds a preset threshold, the program recognizes that a disturbance has occurred and holds the waveform peak, to reduce the effect of disturbance. The waveform analysis program 124 performs calculations involving Pb/Pa, Pc/Pa, Pd/Pa, Pe/Pa, and (Pb−Pc−Pd−Pe)/Pa (aging index) and other analysis values with respect to the Pa to Pe waves (refer to FIG. 5 (A)) included in the pulse waveforms. The arrhythmia detection program 126 detects missing pulses as arrhythmia, based on the pulse intervals of pulse waves. The alert program 128 outputs a corresponding alarm when the result of analysis by the waveform analysis program 124 exceeds a preset threshold, or when arrhythmia is detected by the arrhythmia detection program 126, or the like.

FIG. 5 (A) shows an example of acceleration pulse waves. The horizontal axis of the graph represents time, while the vertical axis represents the pulse wave amplitude detected by the piezoelectric element 30. FIG. 5 (B) is an enlarged view of a pulse waveform in FIG. 5 (A). In this example, Pa through Pe waves are detected and calculations are performed with respect to these waves by the waveform analysis program 124. As shown in FIG. 5 (C), driving wave pressure is applied to the blood vessel BV from the heart side, while reflective wave pressure is applied from the opposite direction, and these wave pressures affect each other synergistically to produce the pulse waves shown in FIG. 5 (B). The meanings of Pa to Pe waves are as follows:
Pa wave: Early systolic positive wave (Systolic forward component of the photoplethysmogram of a finger)
Pb wave: Early systolic negative wave (Same as above)
Pc wave: Mid-systolic re-ascending wave (Systolic rearward component of the finger photoplethysmogram)
Pd wave: Late systolic re-descending wave (Same as above)
Pe wave: Early diastolic positive wave (Diastolic component of the finger photoplethysmogram)

Also, the waveform analysis program 124 calculates the average waveform of acceleration pulse waves and uses the multiple waveform height components included in the acceleration pulse wave, to calculate the wave height ratios of Pb/Pa, Pc/Pa, Pd/Pa, Pe/Pa, (Pb-Pc-Pd-Pe)/Pa, etc. The meanings of these calculation results are described in the following literatures, for example:
(a) Takazawa et al., "Assessment of Vasoactive Agents and Vascular Aging by the Second Derivative of Photoplethysmogram Waveform" Hypertension, August 1998
(b) Junichiro Hashimoto et al., "Pulse wave velocity and the second derivative of the finger photoplethysmogram in treated hypertensive patients: their relationship and associating factors" Journal of Hypertension 2002, Vol 20 No 12

Next, FIG. 5 (D) shows an example of arrhythmia, where no pulse is present at the position indicated by the arrow F5 where there should be a pulse. This is detected by the arrhythmia detection program 126.

FIG. 6 shows an example of a setting menu displayed on the display 104 of the waveform analysis device 100, allowing for selection of a graph to be displayed, selection of an alarm output method, setting of thresholds, etc.

Next, overall operations in this example are explained. Pulse wave signals output from the piezoelectric element 30 are amplified by the instrumentation amplifier 26 and then input to the main board 50. On the main board 50, the signals are further amplified by the programmable amplifier 52 and then converted to digital signals by the A/D converter 53, after which the converted signals are transmitted from the transmitting module 54. The transmitted pulse wave signals are received by the receiving module 62 of the USB dongle 60, and input to the waveform analysis device 100 from the USB interface 64.

At the waveform analysis device 100, the input data is stored as waveform data 112 in the data memory 110. As the noise elimination program 122 is run by the CPU 102, a disturbance exceeding a preset threshold may be found in the waveform data 112, in which case the waveform peak will be held to eliminate the noise. As the waveform analysis program 124 is run by the CPU 102, Pa through Pe waves are detected from the waveforms and also the aforementioned Pb/Pa, Pc/Pa, Pd/Pa, Pe/Pa, (Pb−Pc−Pd−Pe)/Pa, etc., are calculated, and the calculation results are stored in the data memory 110 as calculation data 114 and also displayed on the display 104. In addition, the arrhythmia detection program 126 is run by the CPU 102 to detect arrhythmia. Furthermore, if any of the calculation results exceeds a threshold or arrhythmia is detected, a corresponding alarm is output by the alert program 128 in the form of light or sound.

FIG. 7 shows an example display on the display 104. The average values of respective calculation results are shown at the top. "P.R." indicates the pulse rate, while "A.I." indicates the aging index value. Graphs GA to GF of the calculation results are shown in the middle. The graphs GA, GB, GC, GD, GE, and GF show changes in the P.R. value, Pb/Pa, Pc/Pa, Pd/Pa, Pe/Pa, and (Pb-Pc-Pd-Pe)/Pa, respectively. Pulse waveform G is shown at the bottom of the display 104 in real time. By referencing these graphs of analysis values, it is possible to know the blood vessel hardness (level of arterial sclerosis) and also detect the patient's psychological state in terms of stress and pain and also obtain information on circulatory failure or absence thereof, etc.

As described above, according to this example:
(a) measured pulse waves can be amplified and measured at high sensitivity, while pulse wave analysis values can be calculated and displayed;
(b) changes in the patient's vascular state can be understood in real time during and after surgery or after drug administration, so that proper treatment can be given;
(c) signals exceeding the threshold are held at the peak, to reduce the effect of noise in a favorable manner; and
(d) an alarm is output if arrhythmia occurs or an abnormal analysis value is found, so that appropriate action can be taken.

Example 3

Next, Example 3 of the present invention is explained by referring to FIG. 8. In this example, the aforementioned sensor module 10 is used in a breath-sensing device 200 for driver operating a vehicle. As shown in FIG. 8 (A), a sensing mat (air bag) 206 is provided on a seatbelt 204 in such a way that, when the driver seated in a driver seat 202 of a vehicle wears the seatbelt 204, the sensing mat 206 is sandwiched between the seatbelt and the driver's chest. Then, this sensing mat 206 is connected to the sensor module 10 with a tube 208. As shown in FIG. 1, the sensor module 10 has the cavity 41 where the piezoelectric element 30 is present, formed by the vibration ring 40; accordingly, changes in the internal pressure of the sensing mat 206 are transmitted to this cavity 41.

When the driver breathes, the sensing mat 206, which is sandwiched between the seatbelt 204 and the driver, contracts and expands repeatedly due to breathing. As these repeated contractions and expansions are transmitted to the cavity 41 of the sensor module 10 via the tube 208, the piezoelectric element 30 vibrates and a breath waveform is obtained. FIG. 8 (B) shows an example of breath waveform. From this breath waveform, it is possible to know the state of tension of the driver, etc. It should be noted that, while the sensing mat 206 was explained above as being installed on the seatbelt 204, it may also be installed on the driver outside the clothes using a band, etc.

Example 4

Next, Example 4 of the present invention is explained by referring to FIG. 9. In this example, the aforementioned sensor module 10 is used in a seated-sensing device 300 for a driver operating a vehicle. As shown in FIG. 9 (A), a seatbelt sensing mat 301 and multiple seat sensing mats 302 to 306 are provided over/on a vehicle seat 320. The seatbelt sensing mat 301 is provided on a seatbelt 328, while the seat sensing mat 302 is provided on a headrest 326. The seat sensing mats 303, 304 are provided on a seatback 322, while the seat sensing mats 305, 306 are provided on a seating surface 324.

The sensing mats 301 to 306 are each connected to the cavity 41 of the sensor module 10 with tubes 311 to 316, as shown in FIG. 9 (B), and signals from each main board 50 of each sensor module 10 are input to the waveform analysis device 100 via the USB dongle 60. On the waveform analysis device 100, results of measurement by the sensing mats 301 to 306 are displayed as graphs G1 to G6. The condition of the driver's seating posture can be grasped from these graphs.

Example 5

Next, Example 5 of the present invention is explained by referring to FIG. 10. In the aforementioned examples, the cavity 41 of the sensor module 10 was hollow; with a sensor module 400 shown in FIG. 10 (A), on the other hand, the cavity part is filled with a resin molding 402. The surface of the resin molding 402 forms a bulged part 402A which bulges slightly from the vibration ring 40. This prevents an air layer from being formed along the target such as skin, and also reduces contact between the vibration ring 40 and the target.

A sensor module 410 shown in FIG. 10 (B) represents an example where a vibration plate (or vibration rod) 412 is erected on the board 20 and the piezoelectric element 30 is placed in its vicinity and covered with a resin molding 414. The shape does not matter so long as the vibration plate 412 contacts the target and its vibration is transmitted to the board 20, as shown in this example.

A sensor module 420 in FIG. 10 (C) represents an example of such sensor module provided in a smartphone, tablet PC, or other electronic devices. The sensor module 420 is secured with a waterproof/dustproof sealing material 434 in such a way that a vibration ring 432 on a board 430 is exposed from an enclosure 422 of the electronic device. The board 430 is supported on a motherboard 424 of the electronic device, by solder bumps 426, in a vibratable manner. Vibration waveform signals from the sensor module 420 are captured in the circuit on the motherboard 424.

It should be noted that the present invention is not limited to the aforementioned examples, and various changes may be added to the extent that they do not deviate from the key points of the present invention. For example, the present invention also includes the following:
(1) While the measurement target was pulse waves, breathing, etc., in the aforementioned examples, the target may be any of various other waveforms. For example, vibration waveforms of engines and motors may be analyzed.
(2) While the sensor module and main board were provided separately in the aforementioned examples, the two may be integrated or the waveform analysis device may also be constitutionally integrated. Also, while a USB dongle was used to transmit and receive signals via BLE in the aforementioned examples, the USB dongle is not required so long as the wave analysis device has a function to transmit and receive signals to/from the main board. In addition, not only BLE, but also any of various other standards, may be applied to signal transmission and reception.

(3) The waveform analysis calculation formulas shown in the aforementioned examples are only examples, and various other calculations may be performed as necessary.

(4) While the piezoelectric element 30 and vibration ring 40 were placed on the same side of the board 20 in the aforementioned examples, they may also be provided on different sides.

(5) While a vibration-conveying body was provided separately from the circuit board in the aforementioned examples, this is only an example and the circuit board may structurally serve as a vibration-conveying body. In other words, effects similar to those described in the aforementioned examples can still be achieved by a constitution where a part of the circuit board is caused to contact the target to allow the vibrations of the target to be transmitted to the circuit board, with these vibrations transmitted further to the piezoelectric element provided on the circuit board.

(6) While stainless steel was cited as an example of the material for the vibration ring 40 in Example 1 above, this is also an example and any of various other known conductive materials may be used. Also, the vibration ring 40 need not be entirely formed by a conductive material, and a plastic ring that has been coated with a conductive material may be used, for example.

(7) While the piezoelectric element 30 was rectangular and designed to output waveform signals based primarily on displacement in the lengthwise direction (longitudinal direction) in the aforementioned examples, this is also an example. So long as the piezoelectric element is oval or otherwise shaped so that it has a longitudinal direction, for example, the piezoelectric element will output waveform signals based primarily on displacement in the longitudinal direction.

(8) While the present invention was applied to measurement of human pulse waves in the aforementioned examples, needless to say it can also be used on animals. Additionally, even when the target has body hair and it is contacted by the vibration ring, vibrations can still be introduced to the vibration ring and vibration waveforms can be measured in a favorable manner.

(9) Furthermore, the measurement target need not be a living thing, but it may also be a structure or machinery. In many cases before a structure or machinery fails or breaks, it generates low-frequency vibrations that are different from normal vibrations. For example, a structure or machinery can be inspected in a non-destructive manner by using a vibrator, etc., to apply external vibrations of a certain frequency to the structure or machinery from the outside, and then detect low-frequency vibrations using this sensor. It should be noted that, in this case, a magnet ring may be used to install the sensor and it can also be used as the vibration ring, if the measurement target is made of iron, steel, etc. Also, changes in the atmospheric pressure in the cavity formed between the piezoelectric element and vibration-conveying body may be measured as vibration waveforms using the piezoelectric element.

INDUSTRIAL FIELD OF APPLICATION

According to the present invention, vibration waveforms are measured with a sensor module that uses a piezoelectric element; accordingly, acceleration waveforms can be obtained continuously to perform waveform analysis, which is ideal for medical applications, etc., involving measurement of pulse waves, breathing, etc.

DESCRIPTION OF THE SYMBOLS

10: Sensor module
12, 16: Medical fixing tape
14: Surface fastener
20: Board
22, 23: Electrode land
22A, 23A: Through hole
24: Ground conductor
24A, 24B: Through hole
26: Instrumentation amplifier
30: Piezoelectric element
40: Vibration ring
41: Cavity
50: Main board
52: Programmable amplifier
53: A/D converter
54: Transmitting module
58: Power supply
60: USB dongle
62: Receiving module
64: Interface
100: Waveform analysis device
102: CPU
104: Display
110: Data memory
112: Waveform data
114: Calculation data
120: Program memory
122: Noise elimination program
124: Waveform analysis program
126: Arrhythmia detection program
128: Alert program
200: Breath-sensing device
202: Driver seat
204: Seatbelt
206: Sensing mat
208: Tube
300: Seated sensing device
301: Seatbelt sensing mat
302 to 306: Seat sensing mat
311 to 316: Tube
320: Seat
322: Seatback
324: Seating surface
326: Headrest
328: Seatbelt
400: Sensor module
402: Resin molding
402A: Bulged part
410: Sensor module
412: Vibration plate
414: Resin molding
420: Sensor module
422: Enclosure
424: Motherboard
426: Solder bump
430: Board
432: Vibration ring
434: Waterproof/dustproof sealing material
BD: Skin
BV: Blood vessel
HP: Pulse wave

What is claimed is:

1. A vibration waveform sensor, comprising:
a circuit board having a principal face and a reverse side face opposite to the principal face;
a piezoelectric element provided on the circuit board, that continuously receives vibrations of the circuit board and obtains vibration waveforms, said piezoelectric element having electric connection on the reverse side face of the circuit board for connecting to an amplifier; and
a vibration-conveying body that is a protrusion provided on and protruding from the principal face of the circuit board in a vicinity of the piezoelectric element, and that is configured to contact a target and transmits vibrations of the target to the circuit board,
wherein the vibration-conveying body is electrically conductive and electrically connected to a ground conductor which is provided on the principal face of the circuit board.

2. The vibration waveform sensor according to claim 1, wherein a signal amplifier for amplifying signals of the vibration waveforms obtained from the piezoelectric element, is provided on the circuit board.

3. The vibration waveform sensor according to claim 1, wherein the vibration-conveying body is an electrically conductive ring that has a resin molded in a manner filling an inner space enclosed by the ring and bulges out of the ring.

4. The vibration waveform sensor according to claim 1, wherein the piezoelectric element is shaped in a manner having a longitudinal direction, and the piezoelectric element outputs signals of the vibration waveforms based primarily on displacement in the longitudinal direction.

5. A waveform analysis device comprising a computing unit which performs predefined calculations using vibration waveforms obtained by a vibration waveform sensor to conduct waveform analysis, wherein the vibration waveform sensor comprises: (i) a circuit board; (ii) a piezoelectric element provided on the circuit board, that continuously receives vibrations of the circuit board and obtains vibration waveforms; and (iii) a vibration-conveying body that is configured to contact a target and transmits vibrations of the target to the circuit board,
wherein the vibration waveforms are human pulse waveforms, and an early systolic positive wave height Pa, an early systolic negative wave height Pb, a mid-systolic re-ascending wave height Pc, a late systolic re-descending wave height Pd, and/or an early diastolic positive wave height Pe are/is detected from the waveforms to obtain detected height value(s), and at least one of Pb/Pa, Pc/Pa, Pd/Pa, Pe/Pa, and (Pb−Pc−Pd−Pe)/Pa is calculated using the detected height value(s).

6. The waveform analysis device according to claim 5, which further comprises a noise elimination circuitry for eliminating noise peak values of the vibration waveforms when the peak values exceed a preset threshold.

7. The waveform analysis device according to claim 5, wherein the vibration waveforms are pulse waves and the waveform analysis device further comprises:
a waveform analysis circuitry for performing prescribed calculations with respect to each of multiple waveform components included in the pulse waves;
an arrhythmia detection circuitry for detecting arrhythmia from pulse intervals of the pulse waves; and
an alarm circuitry for outputting an alarm when a result of calculations by the waveform analysis circuitry exceeds a prescribed threshold or when arrhythmia is detected by the arrhythmia detection circuitry.

8. A waveform analysis device comprising a computing unit which performs predefined calculations using vibration waveforms obtained by a vibration waveform sensor to conduct waveform analysis, wherein the vibration waveform sensor comprises: (i) a circuit board that transmits vibrations; (ii) a piezoelectric element installed on the circuit board, that converts vibrations transmitted from the circuit board to electrical signals and outputs the electrical signals as waveform signals to obtain vibration waveforms; and (iii) a vibration-conveying body that is configured to contact a target, detects vibrations introduced by the target on the vibration-conveying body, and transmits the detected vibrations to the circuit board,
wherein the vibration waveforms are human pulse waveforms, and an early systolic positive wave height Pa, an early systolic negative wave height Pb, a mid-systolic re-ascending wave height Pc, a late systolic re-descending wave height Pd, and/or an early diastolic positive wave height Pe are/is detected from the waveforms to obtain detected height value(s), and at least one of Pb/Pa, Pc/Pa, Pd/Pa, Pe/Pa, and (Pb−Pc−Pd−Pe)/Pa is calculated using the detected height value(s).

9. The waveform analysis device according to claim 8, wherein the vibration-conveying body of the waveform sensor is electrically conductive.

10. The waveform analysis device according to claim 8, wherein a signal amplifier for amplifying the waveform signal obtained from the piezoelectric element, is provided on the circuit board of the waveform sensor.

11. The waveform analysis device according to claim 8, wherein the vibration-conveying body of the waveform sensor is an electrically conductive ring that has a resin molded in a manner filling an inner space enclosed by the ring and bulges out of the ring.

12. The waveform analysis device according to claim 8, wherein the piezoelectric element of the waveform sensor is shaped in a manner having a longitudinal direction, and the piezoelectric element outputs the waveform signals based primarily on displacement in the longitudinal direction.

13. The waveform analysis device according to claim 8, which further comprises a noise elimination circuitry for eliminating noise peak values of the vibration waveforms when the peak values exceed a preset threshold.

14. The waveform analysis device according to claim 8, wherein the vibration waveforms are pulse waves and the waveform analysis device further comprises:
a waveform analysis circuitry for performing prescribed calculations with respect to each of multiple waveform components included in the pulse waves;
an arrhythmia detection circuitry for detecting arrhythmia from pulse intervals of the pulse waves; and
an alarm circuitry for outputting an alarm when a result of calculations by the waveform analysis means exceeds a prescribed threshold or when arrhythmia is detected by the arrhythmia detection circuitry.

15. The waveform analysis device according to claim 9, wherein the vibration waveform sensor further comprises a ground conductor which is provided on a principal face of the circuit board and electrically connected to the vibration-conveying body, and is led out to a reverse side face of the circuit board.

* * * * *